United States Patent [19]

Lam

[11] 4,071,317

[45] Jan. 31, 1978

[54] TEST COMPOSITION AND DEVICE FOR DETERMINING PEROXIDATIVELY ACTIVE SUBSTANCES AND PROCESS FOR PREPARING SAME

[75] Inventor: Charles Tak Wai Lam, Elkhart, Ind.

[73] Assignee: Miles Laboratories, Inc., Elkhart, Ind.

[21] Appl. No.: 777,002

[22] Filed: Mar. 14, 1977

[51] Int. Cl.$^2$ ..................... G01N 31/22; G01N 33/16
[52] U.S. Cl. .............................. 23/253 TP; 23/230 B; 252/408
[58] Field of Search ....................... 23/253 TP, 230 B; 252/408

[56] References Cited

U.S. PATENT DOCUMENTS

| | | | |
|---|---|---|---|
| 3,012,976 | 12/1961 | Adams, Jr. et al. | 23/230 B X |
| 3,252,762 | 5/1966 | Adams, Jr. et al. | 23/253 TP |
| 3,853,470 | 12/1974 | Morin et al. | 252/408 X |
| 3,853,471 | 12/1974 | Rittersdorf et al. | 23/253 TP |
| 3,917,452 | 11/1975 | Rittersdorf et al. | 23/230 B |
| 4,017,261 | 4/1977 | Svoboda et al. | 252/408 X |

*Primary Examiner*—Robert M. Reese
*Attorney, Agent, or Firm*—Edward H. Gorman

[57] ABSTRACT

A test composition is disclosed which is useful in determining the presence of a peroxidatively active substance, such as hemoglobin, in a test sample. The composition comprises an organic hydroperoxide, an indicator capable of producing a detectable response in the presence of a peroxide, and a diluent having the structure

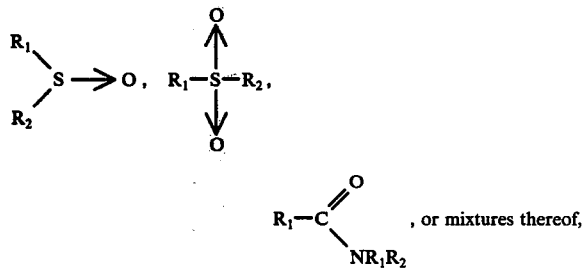

, or mixtures thereof, in which $R_1$ and $R_2$, same or different, are hydrogen, alkyl or alkoxy having 1 to about 6 carbon atoms, or aryl. The method comprises preparing the test composition and incorporating it with a carrier matrix.

40 Claims, No Drawings

TEST COMPOSITION AND DEVICE FOR DETERMINING PEROXIDATIVELY ACTIVE SUBSTANCES AND PROCESS FOR PREPARING SAME

BACKGROUND OF THE INVENTION

1. Field of the Invention

The present invention relates to the detection of constituents in a test sample. More particularly, the invention relates to the qualitative and semi-quantitative analysis of a sample for constituents which possess peroxidative activity.

2. Description of the Prior Art

Many analytical methods are presently available for detecting the presence of peroxidatively active substances in samples such as urine, fecal suspensions, and gastrointestinal contents. Hemoglobin and its derivatives are typical of such "peroxidatively active" substances because they behave in a manner similar to the behavior of the enzyme peroxidase. Such substances have also been referred to as pseudoperoxidases. Peroxidatively active substances are enzyme-like in that they catalyze the redox reaction between peroxides and benzidine, o-tolidine, 3,3',5,5'-tetramethylbenzidine, 2,7-diaminofluorene or similar indicator substances, thereby producing a detectable response such as a color change. Hence, most methods for determining the presence of occult blood in test samples rely on this pseudoperoxidase activity.

Several methods have evolved over the years which rely on enzymelike catalysis of the peroxidic oxidation of color-forming indicators. Primarily these include wet chemical procedures and "dip-and-read" type reagent-bearing strips. Of the former, a typical example is set forth in Richard M. Henry, et al., *Chemical Chemistry Principles and Techniques* (Hagerstown, Maryland: Harper and Row, 1974), pp. 1124–1125. This procedure involves the use of glacial acetic acid (buffer), diphenylamine (indicator), and hydrogen peroxide. While such wet methods have proven analytical ability, they are nevertheless fraught with obvious shortcomings, not the least of which are poor reagent stability and inadequate sensitivity. Inherent to such reagent solutions is a decline in stability (ergo sensitivity) so rapid that fresh reagent solutions must be prepared after several days of storage, a necessity resulting in both excessive time required of analytical personnel, and poor economy because of having to waste costly reagents.

A second method for the determination of peroxidatively active substances, and the one presently preferred by most clinical assayists and analysts, utilizes the so-called "dip and read" reagent strips. Typical of such devices are reagent strips manufactured by the Ames Company Division of Miles Laboratories, Inc. and sold under the name HEMASTIX ®. These comprise, in essence, a porous paper matrix affixed to a plastic strip or handle. The matrix is impregnated with a buffered mixture of an organic hydroperoxide and o-tolidine. Upon immersion in a liquid containing hemoglobin, myoglobin, erythrocytes or other pseudoperoxidases, a blue color develops in the matrix, the intensity of which is proportional to the concentration of the peroxidatively active substance in the sample. Thus, by comparing the color developed in the matrix to a standard color chart, the assayist can determine, on a semi-quantitative basis, the amount of unknown present in the sample.

Hence, the advantages of reagent strips over wet chemistry methods are predominantly twofold: strips are easier to use because neither the preparation of reagents nor the attendant apparatus is required; and greater stability of reagents is afforded, resulting in greater accuracy, sensitivity and economy.

But the inherent advantages of strips over wet chemistry notwithstanding, the characteristics of stability and sensitivity are in need of still further improvement. Whereas these properties in current state-of-the-art strips for determining pseudoperoxidases are greatly enhanced over those of wet chemical methods, there would nevertheless accrue a great advance in the art if such strips could be made even more stable during storage and even more sensitive to peroxidatively active substances. It was towards achieving these improvements that the research activities resulting in the present invention were directed.

At least three attempts at achieving the above-mentioned goals are recorded in the prior art. A recitation in Chemical Abstracts Volume 85, page 186 (1976) describes a two-dip method for preparing reagent strips containing o-tolidine and phenylisopropyl hydroperoxide. In this method a solution is made of the indicator (o-tolidine · 2HCl) and polyvinylpyrrolidone in ethanol. To this solution was added a small amount of surfactant and enough citrate buffer to provide a pH of 3.7. Filter paper strips impregnated with ethyl cellulose were dipped in this solution and dried. The thus-impregnated filter paper was subsequently dipped into a second solution containing 1,4-diazabicyclo [2.2.2]octane, phenylisopropyl hydroperoxide and polyvinylpyrrolidone dissolved in an ethanol-toluene mixture. The thrust of this experiment was to stabilize the peroxide and indicator combination through the use of the bicyclooctane derivative and the polyvinylpyrrolidone.

A second such method is disclosed in U.S. Pat. No. 3,853,471. This patent teaches the use of phosphoric or phosphonic acid amides where the substituent amido groups are primarily N-morpholine radicals.

Besides these attempts, there also exists the disclosure of U.S. Pat. No. 3,252,762 wherein the organic hydroperoxide is physically encapsulated within a colloidal material such as gelatin. Thus, when such a test strip is utilized, the aqueous test sample dissolves the gelatin capsules, thereby freeing the hydroperoxide for further reaction with the indicator in the presence of a peroxidatively active substance.

Each of these prior attempts was aimed at stabilizing the reagents so that the potentially incompatible reactive ingredients (hydroperoxide and indicator) would not prematurely combine and thereby render the test strips less sensitive. Hence, it can be said that the prior art methods were not directed towards the combined objectives of simultaneously enhancing stability and sensitivity, but rather they attempted to preserve existing sensitivity by preventing reagent decomposition during storage.

Another prior art reference which is of interest to the general concepts discussed herein is U.S. Pat. No. 3,236,850. This patent is directed towards stabilizing organic hydroperoxides used as catalysts and oxidizing agents. The patentees in this reference disclose the use of primary, secondary, or tertiary amine salts with organic peroxides. This reference is in no way directed toward reagent test strips.

Upon realizing that none of the above-described methods would achieve the kind of stability and sensitivity desired in a test strip for detecting peroxidatively active substances, the present inventor decided to take a completely different tack. This different approach was discovered during the research which led to the present invention, and resulted in a composition and device which completely fulfilled the desired objectives of increased stability and sensitivity.

But, even more surprisingly, yet another advantage resulted from this work — an improved method for preparing the device presently disclosed whereby the manufacture is dramatically simpler than processes enumerated in the foregoing prior art references — a one-dip method.

SUMMARY OF THE INVENTION

Briefly stated, the present invention relates to a test composition and device for detecting the presence of a peroxidatively active substance in a test sample. The composition is prepared by combining an organic hydroperoxide, an indicator capable of producing a detectable response in the presence of a peroxide and a diluent comprising at least one compound having the structure

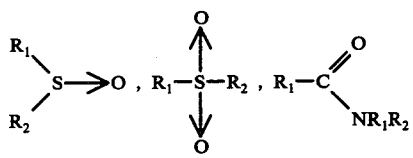

or mixtures thereof, in which $R_1$ and $R_2$, same or different, are hydrogen, alkyl or alkoxy having from 1 to about 6 carbon atoms, or aryl.

The test device is prepared by first preparing the above test composition and then incorporating it with a carrier matrix.

DETAILED DESCRIPTION OF THE INVENTION

The organic hydroperoxide contemplated for use in the test composition can be selected from many well-known organic hydroperoxides. It must, however, be capable of interacting with a peroxidatively active substance in the presence of a peroxidatively-sensitive indicator to produce a detectable response such as a color change or change in the amount of light absorbed or reflected by the test composition. Among hydroperoxides which have been found suitable are t-butyl hyproperoxide, cumene hydroperoxide, diisopropylbenzene hydroperoxide, 2,5-dimethylhexane-2,5-dihydroperoxide, paramenthane hydroperoxide or mixtures thereof. Of these, cumene hydroperoxide has been found to be most preferable.

There exist many indicators which are capable of producing a detectable response in the presence of an organic hydroperoxide and a peroxidatively active substance and which are, therefore, suitable for use in the present invention. For the most part, these include the so-called "benzidine-type" compounds. Typical of these are benzidine, o-tolidine, 3,3',5,5'-tetramethylbenzidine, 2,7-diaminofluorene or mixtures of these in varying proportions.

The diluent compounds which are presently believed to contribute to the increased stability and sensitivity of the present invention have the structures depicted above. Of the compounds included in these generic structures, it has been found that N,N-dimethyl formamide, dimethyl sulfoxide, dimethyl sulfone, or their mixtures are especially suitable. Although these compounds and others within the above generic description enhance stability and sensitivity, it will be appreciated that some may do so to a greater degree than others. Accordingly, it has been found that mixtures of dimethyl sulfone and N,N-dimethyl formamide are most preferable. These compounds correspond to the above structural formulas where $R_1$ and $R_2$ are each methyl. Other diluents found to be operable are benzyl sulfoxide, 4-chlorophenyl sulfone, 4-fluoro-3-nitrophenyl sulfone and others.

The scope of $R_1$ and $R_2$ encompassed by the presently disclosed inventive concepts is broad. Hence, by $R_1$ and $R_2$ are meant substituted or unsubstituted alkyl or alkoxy of 1 to about 6 carbon atoms. Illustrative of the alkyl groups are methyl, ethyl, propyl, isopropyl, n-butyl, isobutyl, t-butyl, sec-butyl, n-pentyl, isopentyl, neopentyl, t-pentyl and other isomers, including those of hexane. These alkyl groups are also illustrative of the alkoxy groups intended as satisfying the foregoing definition of $R_1$ and $R_2$.

Typical of groups with which $R_1$ and $R_2$ may be substituted are amino, nitro, amido, nitrilo, hydroxyl, alkyloxy, halogen, etc.

When $R_1$ and $R_2$ are aryl, the scope is likewise broad and the term aryl, as used herein, includes substituted and unsubstituted aryl groups such as phenyl, benzyl, tolyl, anilino, naphthyl, etc.

The amount of diluent utilized in the presently disclosed composition, device and process can vary widely, and can easily be determined at the laboratory bench. Thus, when the diluent is a liquid such as dimethyl sulfoxide, (see Table I, infra) the amount can vary from about 10% to about 100% based on the volume of diluent added to the composition, compared with the volume of solvent or suspending agent (in the case of Example III, water). A preferred range is about 25% to about 100%.

Likewise, when the diluent is a mixture of more than one of the diluent compounds disclosed herein, the ratio of the amounts of the several compounds used as the diluent can vary broadly, and these, also, can readily be determined in the laboratory.

In a preferred embodiment of the present invention, the composition comprises cumene hydroperoxide, o-tolidine, and a mixture of dimethyl sulfone and N,N-dimethyl formamide.

The test composition is typically prepared by dissolving or suspending portions of each ingredient in water or other suitable suspending agent or solvent. Other suitable solvents include chloroform, methylene chloride, methanol, cyclohexane, the above-mentioned diluents, and mixtures thereof in varying proportions.

The test device can be prepared from a one-dip process. Accordingly, a portion of carrier matrix material is immersed in the solution and dried. Test devices thus prepared exhibit little loss in reactivity even after storage under stress conditions such as about 60° to about 70° C for 1 to 3 days and longer. By way of comparison, test devices were similarly prepared, but without the presence of the diluent. When these strips were stored under substantially identical stress conditions, a dramatic loss in reactivity and sensitivity was observed.

The carrier matrix utilized in forming the test device can take on a multitude of forms. Thus, U.S. Pat. No. 3,846,247 teaches the use of felt, porous ceramic strips, and woven or matted glass fibers. Additionally, U.S.

Pat. No. 3,552,928 teaches the use of wood sticks, cloth, sponge material, and argillaceous substances. The use of synthetic resin fleeces and glass fiber felts as a carrier matrix is suggested in British Pat. No. 1,369,139. Another British Pat. No. 1,349,623, proposes the use of light-permeable meshwork of thin filaments as a cover for an underlying paper matrix. Polyamide fibers are taught in French Pat. No. 2,170,397. These suggestions notwithstanding, however, the material predominantly used in the art as a carrier matrix, and that which is especially suitable for the present invention, is a bibulous paper such as filter paper. It can thus be seen that there is a great deal of leeway in selecting an appropriate material for use as a carrier matrix, and the matrix can take on various physical forms. All of these types are intended as being within the scope of the present invention.

The following examples are provided to further illustrate the concepts and advantages of the presently disclosed invention. They show how to make and use the invention, and present comparative data demonstrating the improved stability and sensitivity it provides. These examples are, however, not to be interpreted as limiting in any way the scope of the invention.

A. TEST COMPOSITION

EXAMPLE I — Preparation of the Test Composition

To a 500 ml (milliliter) beaker were added the following components:

| | | |
|---|---|---|
| chloroform | 100 | ml |
| cumene hydroperoxide | 4.0 | g (grams) |
| o-tolidine | 0.4 | g |
| dimethyl sulfoxide | 25.0 | ml |

The resultant test composition, which was slightly yellow upon combining the above ingredients, was transferred to an Erlenmeyer flask which was stoppered and left on the laboratory bench at room temperature (about 18.3° C) overnight. After one day the test composition had grown only slightly darker than when it was prepared.

EXAMPLE II — Comparison with Example I

A test composition for control purposes, i.e., for comparison with the present invention, was prepared by following the procedure of Example I, except that 25 ml additional chloroform was substituted for the dimethyl sulfoxide. This test composition, without dimethyl sulfoxide, was stoppered in an Erlenmeyer flask and left on the laboratory bench as in Example I (i.e., at 18.3° C for one day). Contrary to the results of Example I, the control composition darkened to almost black, thus indicating the improved stability of the test composition of the present invention due to the diluent.

B. TEST DEVICES

Example III

Six test devices were prepared from six test composition solutions containing varying amounts of dimethyl sulfoxide in accordance with Table I below. These devices were then stressed in order to determine the relative stabilities attributable to various mixtures of dimethyl sulfone and dimethyl sulfoxide.

The six test compositions were all prepared with the following formula:

| | | |
|---|---|---|
| water | 75 | ml |
| trisodium citrate | 3.2 | g |
| citric acid | 4.5 | g |
| triethanolamine borate | 10.0 | g |
| ethylenediamine tetraacetic acid, tetrasodium salt | 0.1 | g |
| dimethyl sulfone | 5.0 | g |
| sodium lauryl sulfate | 1.0 | g |
| 6-methoxyquinoline | 0.5 | g |
| cumene hydroperoxide | 2.0 | g |
| o-tolidine | 0.4 | g |

To each of the six test composition solutions were, added, respectively, the following amounts of dimethyl sulfoxide and methanol:

TABLE I

| Test Composition No. | Dimethyl Sulfoxide (ml) | Methanol (ml) |
|---|---|---|
| 1 | 0 | 75 |
| 2 | 5 | 70 |
| 3 | 10 | 65 |
| 4 | 25 | 50 |
| 5 | 40 | 35 |
| 6 | 60 | 15 |

Test devices were then prepared from each of the above test composition solutions by immersing a piece of Whatmann 3MM filter paper into each solution. The immersed strips of filter paper were withdrawn from their respective solutions, and dried and stressed in an oven at 70° C for 18 hours.

After stressing, each strip was tested in a test solution comprising a 1:1,000,000 dilution of fresh whole blood in urine. The intensity of color developed in each strip provided a comparison means. The results are tabulated in Table II.

TABLE II

| Test Device No.* | Color Rating** |
|---|---|
| 1 | 0 (no color) |
| 2 | 1 (trace) |
| 3 | 3 |
| 4 | 5 |
| 5 | 6 |
| 6 | 7 (almost no loss in reactivity) |

*Test device numbers correspond to the test composition numbers in Table I.
**The color rating was based on a scale of 0 to 8, 8 being the color produced by a freshly prepared, unstressed test device prepared from test composition no. 6 (Table I). A rating of 0 indicates no color formation, a rating of 7 indicates almost no loss of reactivity, and a rating of 1 indicates only trace amounts of color.

It is dramatically apparent from the data in Table II, that sensitivity increases with the amount of diluent (here, dimethyl sulfoxide) used in the test composition formulation.

C. THE EFFECT OF VARIOUS DILUENTS ON STABILITY

Example IV

Eight test compositions were prepared as in Example III, 7 of which contained different diluents and one (control) having no diluent. The purpose of this experiment was to assess the efficacy of various diluents in stabilizing test compositions sensitive to peroxidatively active substances.

A solution was prepared containing the following ingredients:

| | | |
|---|---|---|
| water | 50 | ml |
| trisodium citrate | 3.2 | g |

| | | |
|---|---|---|
| -continued | | |
| citric acid | 2.2 | g |
| sodium lauryl sulfate | 1.0 | g |
| 6-methoxyquinoline | 1.0 | g |
| methanol | 50.0 | ml |
| cumene hydroperoxide | 2.0 | g |
| o-tolidine | 0.4 | g |
| triethanolamine borate | 5.0 | g |

A small aliquot of this solution was added to each of 8 test tubes. Thereafter small amounts of the diluents listed in Table III were respectively added to the test tubes, the test tubes stoppered, and allowed to stand at room temperature on the laboratory bench for one week. At the end of the week, the test tubes were examined for relative darkening in color, the darker the color, the less stable the test composition. The results are given in Table III in order of decreasing stability (i.e., test composition 1 being most stable and test composition 8 being least stable).

TABLE III

| Test Composition No. | Diluent |
|---|---|
| 1 | dimethyl sulfoxide |
| 2 | N,N-dimethyl formamide |
| 3 | dimethyl sulfone |
| 4 | benzyl sulfoxide |
| 5 | 4-chlorophenyl sulfone |
| 6 | 4-fluoro-3-nitrophenyl sulfone |
| 7 | 2-imidazolidone |
| 8(control) | none |

In Table III, samples 1 and 2 were most stable, solution 3 less so, but nevertheless good stability, solutions 4–7 were moderately stable and solution 8, the control, was far less stable than solutions 1–7.

D. PREFERRED EMBODIMENT

Example V

This example illustrates a preferred embodiment of the presently disclosed test device.

A test composition was prepared in a beaker by mixing the following ingredients, in the following order, with stirring:

| | | |
|---|---|---|
| water | 75 | ml. |
| trisodium citrate | 3.2 | g |
| citric acid | 4.15 | g |
| triethanolamine borate | 10.0 | g |
| ethylenediaminetetraacetic acid, tetrasodium salt | 0.1 | g |
| sodium lauryl sulfate | 1.5 | g |
| dimethyl sulfone | 10.0 | g |
| 6-methoxyquinoline | 0.6 | g |
| N,N-dimethyl formamide | 75 | ml |
| cumene hydroperoxide | 3.0 | g |
| o-tolidine | 0.8 | g |

Strips of Whatman 3MM filter paper were immersed in the above composition and dried for about 11 minutes at about 90° to 92° C. The dried strips were then mounted on plastic handles using double-faced adhesive tape.

In order to assess stability and sensitivity, some of the strips were stressed by being stored at 70° C for one day. Others were stressed by storing at 40° C for 12 weeks. Both sets of strips turned a blue/green color when immersed in a 1:1 × 10⁶ dilution of whole blood in urine, thus evidencing excellent stability and sensitivity after stressing.

What is claimed is:

1. A process for preparing a test device for determining the presence of a peroxidatively active substance in a sample, said process comprising the steps of
    a. preparing a test composition by combining an organic hydroperoxide, an indicator capable of producing a detectable response in the presence of a peroxide, and a diluent comprising a compound having the structure

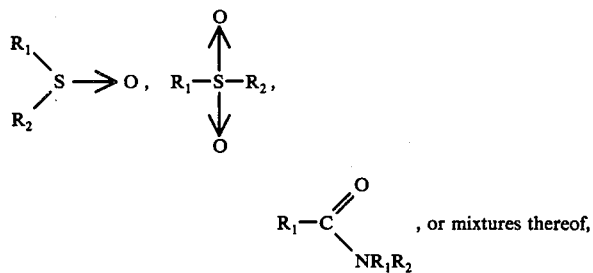

, or mixtures thereof, in which $R_1$ and $R_2$, same or different, are hydrogen, alkyl or alkoxy having 1 to about 6 carbon atoms, or aryl, and
    b. incorporating said test composition with a carrier matrix.
2. The process of claim 1 in which said diluent is dimethyl sulfoxide, dimethyl sulfone, N,N-dimethyl formamide, benzyl sulfoxide, 4-chlorophenyl sulfone, 4-fluoro-3-nitrophenyl sulfone or mixtures thereof.
3. The process of claim 1 wherein said diluent is a mixture of dimethyl sulfone and N,N-dimethyl formamide.
4. The process of claim 1 in which the indicator is benzidene, o-tolidine, 3,3',5,5'-tetramethylbenzidine, 2,7-diaminofluorene or mixtures thereof.
5. The process of claim 1 in which the organic hydroperoxide is t-butyl hydroperoxide, cumene hydroperoxide, diisopropylbenzene hydroperoxide, 2,5-dimethylhexane-2,5-dihydroperoxide, paramenthane hydroperoxide or mixtures thereof.
6. The process of claim 1 in which the organic hydroperoxide is cumene hydroperoxide.
7. The process of claim 6 in which said diluent is a mixture of dimethyl sulfone and N,N-dimethyl formamide.
8. The process of claim 6 in which said diluent is dimethyl sulfoxide, dimethyl sulfone, N,N-dimethyl formamide, benzyl sulfoxide, 4-chlorophenyl sulfone, 4-fluoro-3-nitrophenyl sulfone or mixtures thereof.
9. The process of claim 8 in which the indicator is benzidine, o-tolidine, 3,3',5,5'-tetramethylbenzidine, 2,7-diaminofluorene or mixtures thereof.
10. A process for preparing a test device capable of determining the presence of a peroxidatively active substance in a sample comprising the steps of
    a. preparing a test composition by combining cumene hydroperoxide, o-tolidine, dimethyl sulfone, and N,N-dimethyl formamide,
    b. forming a mixture from said test composition and a suitable solvent,
    c. contacting a carrier matrix with said mixture thereby incorporating the matrix with the test composition and,
    d. drying said carrier matrix.
11. A test composition for determining the presence of a peroxidatively active substance in a sample, the composition comprising an organic hydroperoxide, an indicator capable of producing a detectable response in the presence of a peroxide, and a diluent comprising a compound having the structure

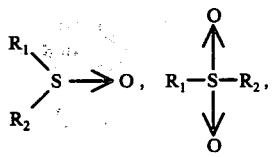

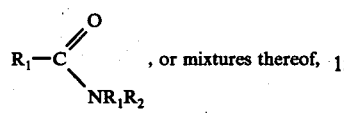

in which $R_1$ and $R_2$, same or different are hydrogen, alkyl or alkoxy having 1 to about 6 carbon atoms or aryl.

12. The composition of claim 11 in which the diluent is dimethyl sulfoxide, dimethyl sulfone, N,N-dimethyl formamide, benzyl sulfoxide, 4-chlorophenyl sulfone, 4-fluoro-3-nitrophenyl sulfone or mixtures thereof.

13. The composition of claim 11 in which the diluent is a mixture of dimethyl sulfone and N,N-dimethyl formamide.

14. The composition of claim 11 in which the indicator is benzidine, o-tolidine, 3,3',5,5'-tetramethylbenzidine, 2,7-diaminofluorene or mixtures thereof.

15. The composition of claim 11 in which the organic hydroperoxide is t-butyl hydroperoxide, cumene hydroperoxide, diisopropylbenzene hydroperoxide, 2,5-dimethylhexane-2,5-dihydroperoxide, paramenthane hydroperoxide or mixtures thereof.

16. The composition of claim 11 in which the organic hydroperoxide is cumene hydroperoxide.

17. The composition of claim 16 in which the diluent is a mixture of dimethyl sulfone and N,N-dimethyl formamide.

18. The composition of claim 16 in which the diluent is dimethyl sulfoxide, dimethyl sulfone, N,N-dimethyl formamide, benzyl sulfoxide, 4-chlorophenyl sulfone, 4-fluoro-3-nitrophenyl sulfone or mixtures thereof.

19. The composition of claim 18 in which the indicator is benzidine, o-tolidine, 3,3',5,5'-tetramethylbenzidine, 2,7-diaminofluorene or mixtures thereof.

20. A test composition for determining the presence of a peroxidatively active substance in a sample, the composition comprising cumene hydroperoxide, o-tolidine, dimethyl sulfone and N,N-dimethyl formamide.

21. A test device for determining the presence of a peroxidatively active substance in a sample, the device having a carrier matrix incorporated with a test composition comprising an organic hydroperoxide, an indicator capable of producing a detectable response in the presence of a peroxide, and a diluent comprising a compound having the structure

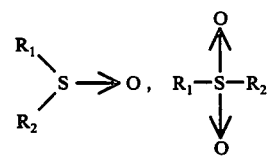

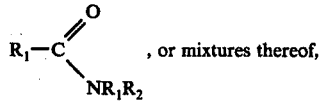

in which $R_1$ and $R_2$ same or different, are hydrogen, alkyl or alkoxy having 1 to about 6 carbon atoms or aryl.

22. The device of claim 21 in which the diluent is dimethyl sulfoxide, dimethyl sulfone, N,N-dimethyl formamide, benzyl sulfoxide, 4-chlorophenyl sulfone, 4-fluoro-3-nitrophenyl sulfone or mixtures thereof.

23. The test device of claim 21 in which the diluent is a mixture of dimethyl sulfone and N,N-dimethyl formamide.

24. The test device of claim 21 in which the indicator is benzidine, o-tolidine, 3,3',5,5'-tetramethylbenzidine, 2,7-diaminofluorene or mixtures thereof.

25. The test device of claim 21 in which the organic hydroperoxide is t-butyl hydroperoxide, cumene hydroperoxide, diisopropylbenzene hydroperoxide, 2,5-dimethylhexane-2,5-dihydroperoxide, paramenthane hydroperoxide or mixtures thereof.

26. The test device of claim 21 in which the organic hydroperoxide is cumene hydroperoxide.

27. The device of claim 26 in which the diluent is a mixture of dimethyl sulfone and N,N-dimethyl formamide.

28. The device of claim 26 in which the diluent is dimethyl sulfoxide, dimethyl sulfone, N,N-dimethyl formamide, benzyl sulfoxide, 4-chlorophenyl sulfone, 4-fluoro-3-nitrophenyl sulfone or mixtures thereof.

29. The device of claim 28 in which the indicator is benzidine, o-tolidine, 3,3',5,5'-tetramethylbenzidine, 2,7-diaminofluorene or mixtures thereof.

30. A test device for determining the presence of a peroxidatively active substance in a sample, the composition comprising cumene hydroperoxide, o-tolidine, dimethyl sulfone and N,N-dimethyl formamide.

31. A test device for determining the presence of a peroxidatively active substance in a sample, said device being prepared by the steps of a. preparing a test composition by combining an organic hydroperoxide, an indicator capable of producing a detectable response in the presence of a peroxide, and a diluent comprising a compound having the structure

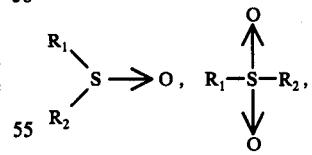

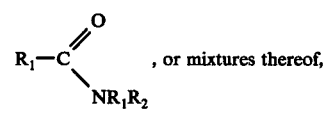

in which $R_1$ and $R_2$, same or different, are hydrogen, alkyl or alkoxy having 1 to about 6 carbon atoms, or aryl, and b. incorporating said test composition with a carrier matrix.

32. The device of claim 31 in which said diluent is dimethyl sulfoxide, dimethyl sulfone, N,N-dimethyl formamide, benzyl sulfoxide, 4-chlorophenyl sulfone, 4-fluoro-3-nitrophenyl sulfone or mixtures thereof.

33. The device of claim 31 in which said diluent is a mixture of dimethyl sulfone and N,N-dimethyl formamide.

34. The device of claim 31 in which the indicator is benzidine, o-tolidine, 3,3',5,5'-tetramethylbenzidine, 2,7-diaminofluorene or mixtures thereof.

35. The device of claim 31 in which the organic hydroperoxide is t-butyl hydroperoxide, cumene hydroperoxide, diisopropylbenzene hydroperoxide, 2,5-dimethylhexane-2,5-dihydroperoxide, paramenthane hydroperoxide or mixtures thereof.

36. The device of claim 31 in which the organic hydroperoxide is cumene hydroperoxide.

37. The device of claim 36 in which said diluent is a mixture of dimethyl sulfone and N,N-dimethyl formamide.

38. The device of claim 36 in which said diluent is dimethyl sulfoxide, dimethyl sulfone, N,N-dimethyl formamide, benzyl sulfoxide, 4-chlorophenyl sulfone, 4-fluoro-3-nitrophenyl sulfone or mixtures thereof.

39. The device of claim 38 in which the indicator is benzidine, o-tolidine, 3,3',5,5'-tetramethylbenzidine, 2,7-diaminofluorene or mixtures thereof.

40. A test device for determining the presence of a peroxidatively active substance in a sample, said device being prepared by the steps of
   a. preparing a test composition by combining cumene hydroperoxide, o-tolidine, dimethyl sulfone, and N,N-dimethyl formamide,
   b. forming a mixture from said test composition and a suitable solvent,
   c. contacting a carrier matrix with said mixture thereby incorporating the matrix with the test composition and,
   d. drying said carrier matrix.

* * * * *